(12) United States Patent
Wang et al.

(10) Patent No.: US 9,000,932 B2
(45) Date of Patent: Apr. 7, 2015

(54) HUMIDITY SENSING FUNCTION FOR A DISPLAY DEVICE

(71) Applicant: E Ink Holdings Inc., Hsinchu (TW)

(72) Inventors: Chih-Hsuan Wang, Hsinchu (TW); Chia-Chun Yeh, Hsinchu (TW); Ted-Hong Shinn, Hsinchu (TW)

(73) Assignee: E Ink Holdings Inc., Hsinchu (TW)

( * ) Notice: Subject to any disclaimer, the term of this patent is extended or adjusted under 35 U.S.C. 154(b) by 102 days.

(21) Appl. No.: 13/742,374

(22) Filed: Jan. 16, 2013

(65) Prior Publication Data

US 2013/0265166 A1   Oct. 10, 2013

(30) Foreign Application Priority Data

Apr. 10, 2012 (TW) .............................. 101112642 A

(51) Int. Cl.
| | | |
|---|---|---|
| G01N 27/00 | (2006.01) | |
| G01N 5/02 | (2006.01) | |
| H01L 51/40 | (2006.01) | |
| G01N 27/04 | (2006.01) | |
| G01K 7/01 | (2006.01) | |
| G01N 27/12 | (2006.01) | |
| G01K 7/16 | (2006.01) | |

(52) U.S. Cl.
CPC ................ *G01N 27/048* (2013.01); *G01K 7/01* (2013.01); *G01N 27/121* (2013.01); *G01K 7/16* (2013.01)

(58) Field of Classification Search
None
See application file for complete search history.

(56) References Cited

U.S. PATENT DOCUMENTS

| | | | |
|---|---|---|---|
| 4,464,647 A | | 8/1984 | Yokomizo et al. |
| 4,638,346 A | * | 1/1987 | Inami et al. .................... 257/253 |
| 7,571,637 B2 | * | 8/2009 | Chen et al. ........................ 73/73 |
| 2009/0107220 A1 | * | 4/2009 | Chen et al. ........................ 73/73 |
| 2010/0071460 A1 | | 3/2010 | Fleischer et al. |
| 2010/0188354 A1 | * | 7/2010 | Tamura .......................... 345/173 |
| 2010/0307238 A1 | | 12/2010 | Van Popta et al. |
| 2011/0148835 A1 | * | 6/2011 | Yamazaki ..................... 345/207 |
| 2012/0032876 A1 | * | 2/2012 | Tabe .............................. 345/156 |
| 2012/0327141 A1 | * | 12/2012 | Yoshida ......................... 345/690 |
| 2013/0187945 A1 | * | 7/2013 | Aragaki et al. ............... 345/619 |
| 2013/0235024 A1 | * | 9/2013 | Sato et al. ...................... 345/212 |
| 2014/0104515 A1 | * | 4/2014 | Golovchenko et al. .......... 349/12 |

FOREIGN PATENT DOCUMENTS

| | | |
|---|---|---|
| CN | 101436370 | 5/2009 |
| TW | 200947089 | 11/2009 |
| TW | 201033960 | 9/2010 |

OTHER PUBLICATIONS

"Office Action of Taiwan Counterpart Application", issued on Jul. 25, 2014, p. 1-p. 8.

* cited by examiner

*Primary Examiner* — Julie Lieu
(74) *Attorney, Agent, or Firm* — Jianq Chyun IP Office

(57) ABSTRACT

An electric apparatus including a display and a process unit is provided. The display has an active area and a peripheral area. The display panel including an active device array substrate, an opposite substrate opposite to the active device array substrate and a display medium between the active device array substrate and the opposite substrate. The active device array substrate has a plurality of active devices disposed in the active area and a humidity sensor disposed in the peripheral area. The humidity sensor is a thin film transistor having a metal oxide semiconductor layer. The process unit is electrically connected to the humidity sensor. The process unit calculates a humidity value according to a sensing current from the humidity sensor.

10 Claims, 4 Drawing Sheets

HUMIDITY SENSING FUNCTION FOR A DISPLAY DEVICE

CROSS-REFERENCE TO RELATED APPLICATION

This application claims the priority benefit of Taiwan application serial no. 101112642, filed on Apr. 10, 2012. The entirety of the above-mentioned patent application is hereby incorporated by reference herein and made a part of this specification.

BACKGROUND OF THE INVENTION

1. Field of the Invention

The invention is related to an electric apparatus, and more particularly to an electric apparatus having a humidity sensing function.

2. Description of Related Art

Humidity indicator card is a common simple-type indicator for determining if humidity of an environment exceeds a normal value. However, humidity indicator card requires observation by a user to obtain if humidity of an environment exceeds normal. Therefore, humidity of an environment may exceed normal for a period before being noticed; in that case, the object monitored by such humidity indicator card may have had been damaged. In addition, humidity indicator card contains several polluting chemical components, thereby failing to comply with the European Union (EU)'s environmental protection requirements. As a result, application range of humidity indicator card is limited.

U.S. Pat. No. 4,638,346 discloses a field effect transistor-type moisture sensor. US20100071460 discloses that characteristics of a channel layer of a field effect transistor may be influenced by humidity of an environment. US20100307238 discloses a field effect transistor-type humidity sensor, which changes its capacitance parameters according to changes in humidity so as to achieve the purpose of humidity detection. U.S. Pat. No. 4,464,647 discloses a metal oxide semiconductor humidity sensor. U.S. Pat. No. 7,571,637 discloses a real-time moisture detection circuitry.

SUMMARY OF THE INVENTION

The invention provides an electric apparatus able to sense humidity.

The invention provides an electric apparatus including a display and a process unit. The display has an active area and a peripheral area connected to the active area. The display includes an active device array substrate, an opposite substrate opposite to the active device array substrate, and a display medium between the active device array substrate and the opposite substrate. The active device array substrate has a plurality of active devices disposed in the active area and a humidity sensor disposed in the peripheral area. The humidity sensor is a thin film transistor having a first metal oxide semiconductor layer. The process unit is electrically connected to the humidity sensor. The process unit calculates a humidity value according to a sensing current from the humidity sensor.

In an embodiment of the invention, the active device array substrate further has a temperature sensor disposed in the peripheral area. The temperature sensor is electrically connected to the process unit. The process unit calculates a temperature of the active device array substrate according to characteristics of the temperature sensor.

In an embodiment of the invention, the temperature sensor is a metal wire surrounding the active area, and the process unit calculates the temperature of the active device array substrate according to a resistance value of the metal wire.

In an embodiment of the invention, each of the active devices has a second gate, a second metal oxide semiconductor layer overlapping with the second gate, and a second source and a second drain disposed at two opposite ends of the second metal oxide semiconductor layer and connected to the second metal oxide semiconductor layer. The metal wire and the second gate or the second source belong to the same film layer.

In an embodiment of the invention, the humidity sensor further has a first gate overlapping with the first metal oxide semiconductor layer, and a first source and a first drain disposed at two opposite ends of the first metal oxide semiconductor layer and connected to the first metal oxide semiconductor layer.

In an embodiment of the invention, the process unit provides a first gate voltage and a first source voltage respectively to the first gate of the humidity sensor and the first source of the humidity sensor according to the temperature of the active device array substrate. The process unit calculates the humidity value according to the sensing current, the first gate voltage, the first source voltage, and the temperature of the active device array substrate, wherein the sensing current is transmitted to the first drain through the first metal oxide semiconductor layer.

In an embodiment of the invention, the first gate and the second gate belong to the same film layer. The first metal oxide semiconductor layer and the second metal oxide semiconductor layer belong to the same film layer. The first source, the first drain, the second source and the second drain belong to the same film layer.

In an embodiment of the invention, the active device array substrate further has a passivation layer. The passivation layer covers the active devices and exposes the first metal oxide semiconductor layer of the humidity sensor.

In an embodiment of the invention, the electric apparatus further includes a warning indicator electrically connected to the humidity sensor. The humidity sensor makes corresponding reactions according to a value of the sensing current from the humidity sensor.

In an embodiment of the invention, the warning indicator includes an indicator light or a buzzer.

In an embodiment of the invention, the electric apparatus further includes a protection system electrically connected to the humidity sensor. The protection system is activated or deactivated according to the value of the sensing current from the humidity sensor.

In an embodiment of the invention, the protection system is an air extractor.

Based on the above, the electric apparatus according to an embodiment of the invention has dual functions of displaying and sensing humidity of an environment by having a thin film transistor having a metal oxide semiconductor layer as a humidity sensor.

In order to make the aforementioned features and advantages of the invention more comprehensible, embodiments accompanied with figures are described in detail below.

DESCRIPTION OF THE EMBODIMENTS

Figure 1:
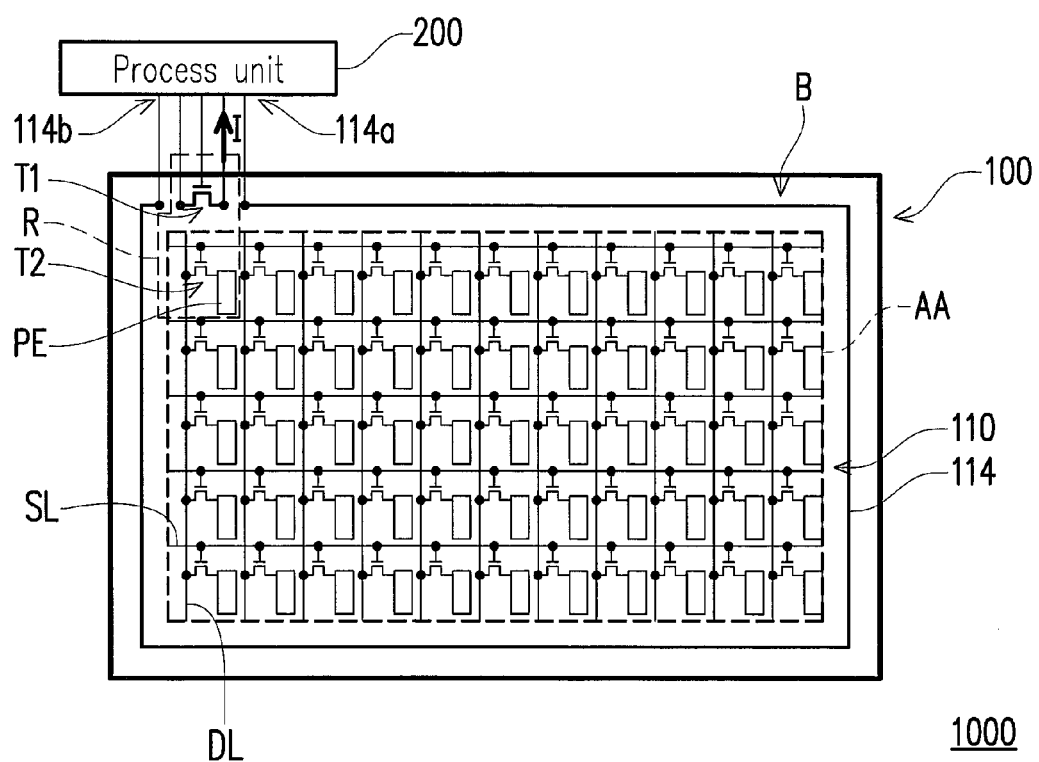
FIG. 1 is a schematic drawing of an electric apparatus according to an embodiment of the invention.
Figure 2:
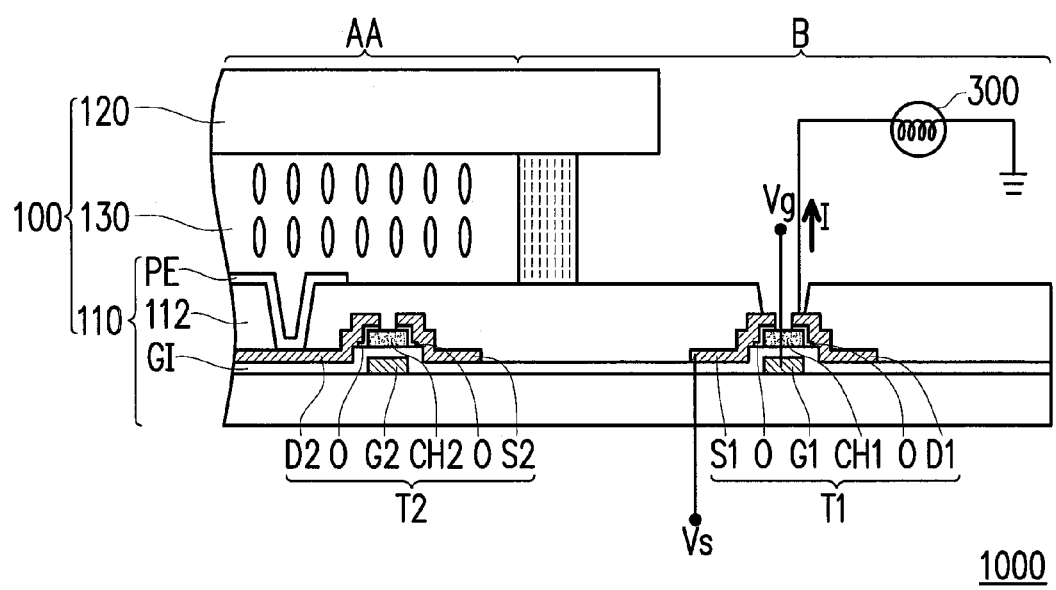
FIG. 2 illustrates a cross section of a local area R in FIG. 1.

FIG. 1 is a schematic drawing of an electric apparatus according to an embodiment of the invention. It is to be noted opposite substrate and display medium are not illustrated in FIG. 1 for clarification purposes. FIG. 2 illustrates a cross section of a local area R in FIG. 1. Referring to FIG. 1 and FIG. 2, an electric apparatus 1000 of this embodiment includes a display 100 and a process unit 200 (illustrated in FIG. 1). The display 100 has an active area AA and a peripheral area B connected to the active area AA. The active area AA refers to an area having a display function in the display 100, while the peripheral area B refers to an area not having a display function in the display 100. In this embodiment, the active area AA is, for example, a rectangular area, and the peripheral area B is, for example, a square area surrounding the active area AA. However, the scope of the invention is not limited thereto. The active area AA and the peripheral area B may be designed in appropriate shapes depending on actual needs.

As shown in FIG. 2, the display 100 of this embodiment includes an active device array substrate 110, an opposite substrate 120, and a display medium 130 between the active device array substrate 110 and the opposite substrate 120. In this embodiment, the display medium 130 is, for example, liquid crystal, and the opposite substrate 120 is, for example, a color filter substrate. However, the scope of the invention is not limited thereto. In other embodiments, the display medium 130 may be a microcapsule having electrophoresis particles, or an organic light-emitting layer, and the opposite substrate 120 may be a light transmissive substrate. The opposite substrate 120 is made of such as glass, quartz, organic polymer, or other suitable materials.

As shown in FIG. 1 and FIG. 2, the active device array substrate 110 of this embodiment has a plurality of active devices T2 disposed in the active area AA and a humidity sensor T1 disposed in the peripheral area B. In particular, the humidity sensor T1 is a thin film transistor (TFT) having a first metal oxide semiconductor layer CH1. The active device array substrate 110 further has a pixel electrode PE electrically connected to the plurality of active devices T2. The active devices T2 and the pixel electrode PE are used for driving the display medium 130, and the humidity sensor T1 is used for monitoring humidity of an environment.

In this embodiment, manufacturing processes of the humidity sensor T1 and the active devices T2 are integrated. In other words, each of the film layers of the humidity sensor T1 and its corresponding film layer of the active devices T2 are made of the same material. The details are explained hereinafter with reference to FIG. 2. As shown in FIG. 2, the humidity sensor T1 of this embodiment has not only the first metal oxide semiconductor layer CH1, but also a first gate G1 overlapping with the first metal oxide semiconductor layer CH1, and a first source S1 and a first drain D1 disposed at two opposite ends of the first metal oxide semiconductor layer CH1 and connected to the first metal oxide semiconductor layer CH1. Each of the active devices T2 has a second gate G2, a second metal oxide semiconductor layer CH2 overlapping with the second gate G2, and a second source S2 and a second drain D2 disposed at two opposite ends of the second metal oxide semiconductor layer CH2 and connected to the second metal oxide semiconductor layer CH2. The second source S2 is electrically connected to a data line DL (illustrated in FIG. 1), and the second drain D2 is electrically connected to a scan line SL (illustrated in FIG. 1).

In this embodiment, the first gate G1, the second gate G2 and the scan line SL are manufactured together. In other words, the first gate G1, the second gate G2 and the scan line SL belong to the same film layer and are made of the same material. The first gate G1, the second gate G2 and the scan line SL are generally made of metal. However, the scope of the invention is not limited thereto. According to other embodiments, the first gate G1, the second gate G2 and the scan line SL may be made of other conductive materials, such as alloy, nitride of metal material, oxide of metal material, nitrogen oxide of metal material, or stack layers of metal material and other conductive materials.

In this embodiment, the first metal oxide semiconductor layer CH1 and the second metal oxide semiconductor layer CH2 are manufactured together. In other words, the first metal oxide semiconductor layer CH1 and the second metal oxide semiconductor layer CH2 belong to the same film layer and are made of the same material. The first metal oxide semiconductor layer CH1 and the second metal oxide semiconductor layer CH2 are made of material selected from a group consisting of indium gallium zinc oxide (IGZO), indium zinc oxide (IZO), indium gallium oxide (IGO), zinc oxide (ZnO), cadmium oxide, germanium oxide ($2CdO.GeO_2$), nickel cobalt oxide ($NiCo_2O_4$) and combinations thereof. In addition, as shown in FIG. 2, between the first metal oxide semiconductor layer CH1 (or the second metal oxide semiconductor layer CH2) and the first gate G1 (the second gate G2), an insulating layer GI is disposed. The insulating layer GI is made of inorganic material (such as silicon oxide, silicon nitride, silicon oxynitride, or stack layers of at least two of the above materials), organic material, or a combination of the above.

In this embodiment, the first source S1, the first drain D1, the second source S2, the second drain D2 and the data line DL are manufactured together. In other words, the first source S1, the first drain D1, the second source S2, the second drain D2 and the data line DL belong to the same film layer and are made of the same material. The material suitable for the first source S1, the first drain D1, the second source S2, the second drain D2 and the data line DL is similar to that for the first gate G1, and thus an explanation thereof is omitted. In addition, the first source S1 and the first drain D1 (or the second source S2 and the second drain D2) may be connected to the first metal oxide semiconductor layer CH1 (or the second metal oxide semiconductor layer CH2) through an ohmic contact layer O to achieve a better performance of the humidity sensor T1 (or the active devices T2).

It is to be noted that in FIG. 2, the humidity sensor T1 and the active devices T2 are bottom gate TFTs for exemplary purposes. However, the invention does not intend to limit the forms of the humidity sensor T1 and the active devices T2. In other embodiments, the active devices T2 (or the humidity sensor T1) may be a top gate TFT or in other appropriate forms.

In addition, as shown in FIG. 2, the active device array substrate 110 of this embodiment optionally includes a passivation layer 112. The passivation layer 112 covers the active devices T2 and the humidity sensor T1. However, to achieve a better effect of humidity detection, the passivation layer 112 may at least expose the first metal oxide semiconductor layer CH1 of the humidity sensor T1, such that the first metal oxide semiconductor layer CH1 is in contact with environmental media, thereby achieving a better sensitivity of the humidity sensor T1 in detecting humidity.

As shown in FIG. 1, the active device array substrate 110 of this embodiment further has a temperature sensor 114 disposed in the peripheral area B. The temperature sensor 114 is electrically connected to the process unit 200. The process unit 200 calculates a temperature of the active device array substrate 110 according to characteristics of the temperature sensor 114. Specifically, in this embodiment, the temperature sensor 114 is a metal wire surrounding the active area AA. Two ends 114a and 114b of the metal wire are each electrically connected to the process unit 200. The process unit 200 calculates the temperature of the active device array substrate 110 according to a resistance value of the metal wire. It is worth noting that the metal wire is manufactured together with the active devices T2 disposed in the active area AA. Specifically, the metal wire is manufactured together with the second gate G2 of the active devices T2, or with the second source S2 and the second drain D2 of the active devices T2. In other words, the metal wire are made of the same material as the second gate G2 of the active devices T2, or as the second source S2 and the second drain D2 of the active devices T2.

As shown in FIG. 1, the process unit 200 of this embodiment is electrically connected to the humidity sensor T1. The process unit 200 calculates a humidity value according to a sensing current I from the humidity sensor T1. The humidity value is used to represent the humidity of the environment where the electric apparatus 1000 of this embodiment is. Specifically, in this embodiment, the process unit 200 first provides a first gate voltage and a first source voltage respectively to the first gate G1 and the first source S1 of the humidity sensor T1 according to the temperature of the active device array substrate 110. Then, the process unit 200 receives the sensing current I transmitted to the first drain D1 through the first metal oxide semiconductor layer CH1. After that, the process unit 200 calculates the humidity value according to a value of the sensing current I, the first gate voltage, the first source voltage, and the temperature of the active device array substrate 110. More specifically, the process unit 200 is embedded with a look up table. The process unit 200 looks up a corresponding humidity value in the look up table and according to the value of the sensing current I, the first gate voltage, the first source voltage, and the temperature of the active device array substrate 110.

Figure 3:
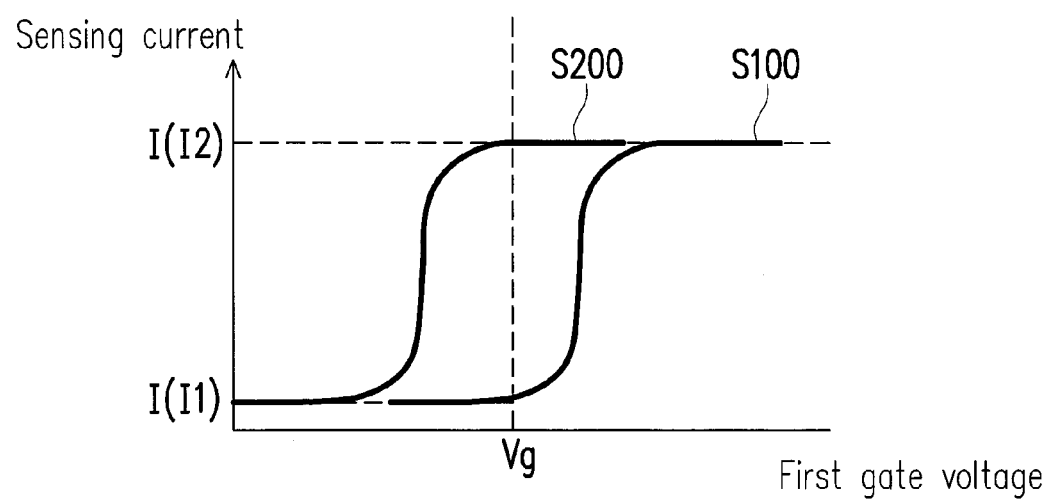
FIG. 3 shows relationships between first source voltage and sensing current of the humidity sensor in FIG. 1 under different humidity conditions.

Again referring to FIG. 2, the electric apparatus 1000 of this embodiment further includes a warning indicator 300. The warning indicator 300 is electrically connected to the humidity sensor T1. The warning indicator 300 makes corresponding reactions according to the value of the sensing current I from the humidity sensor T1. The details are explained hereinafter with reference to FIG. 2 and FIG. 3. FIG. 3 illustrates relationships between first source voltage and sensing current of the humidity sensor in FIG. 1 under different humidity conditions. First, referring to FIG. 2, specifically, the first gate G1 and the first source S1 of the humidity sensor T1 are respectively provided with a first gate voltage Vg and a first source voltage Vs. Referring to FIG. 3, under low humidity (such as 25%/25° C.), the relationship between first gate voltage and sensing current is as shown by a curve S100 in FIG. 3. At this time, the sensing current I (I1) is close to 0, and the warning indicator 300 would not be activated. Under high humidity (such as 60%/25° C.), the relationship between first gate voltage and sensing current is as shown by a curve S200 in FIG. 3. Compared to the curve S100, the curve S200 moves toward the direction of the first gate voltage. At this time, in a state that the first gate G1 remains being provided with a fixed first gate voltage Vg, the sensing current I (I2) is much greater than 0, and the warning indicator 300 would be activated. In this embodiment, the warning indicator 300 is, for example, an indicator light. When a humidity value of the environment where the electric apparatus 1000 is greater than a predetermined value, the indicator light lights up to actively notify a user to take appropriate action. However, the scope of the invention is not limited thereto. In other embodiments, the warning indicator 300 may be a buzzer. When a humidity value of the environment where the electric apparatus 1000 is greater than a predetermined value, the buzzer buzzes to actively notify a user to take appropriate action.

Figure 4:
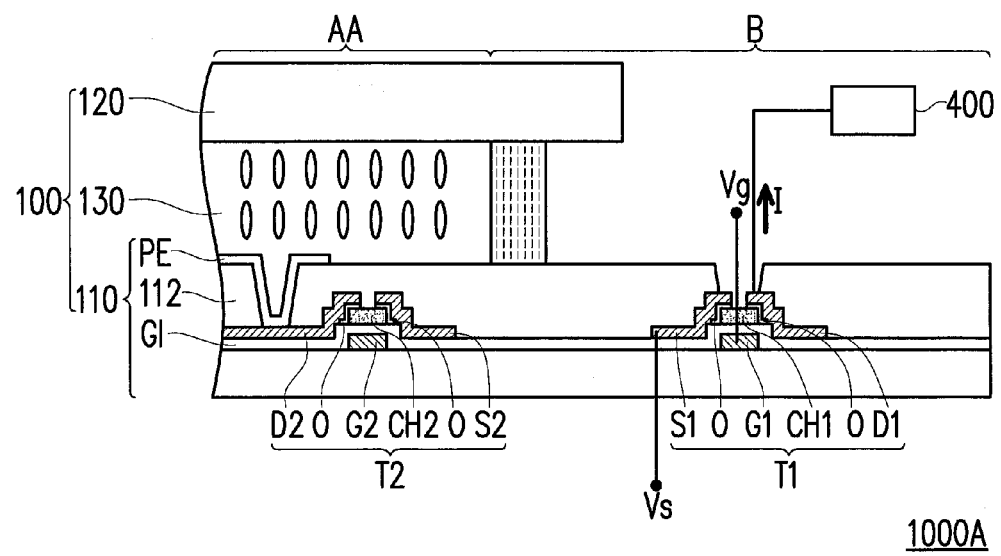
FIG. 4 is a schematic drawing of an electric apparatus according to another embodiment of the invention.

FIG. 4 is a schematic drawing of an electric apparatus according to another embodiment of the invention. Referring to FIG. 4, the electric apparatus 1000A of this embodiment is similar to the electric apparatus 1000 in FIG. 1, and thus the same reference numbers are used for the same elements. The electric apparatus 1000A and the electric apparatus 1000 are different in that the electric apparatus 1000A further includes a protection system 400 electrically connected to the humidity sensor T1. The protection system 400 is activated or deactivated according to a value of the sensing current I from the humidity sensor T1. In this embodiment, the protection system 400 is an air extractor. Similar to the previous paragraph, under low humidity (such as 25%/25° C.), the sensing current I from the first drain D1 is close to 0, and at this time, the air extractor is in a state of deactivation; under high humidity (such as 60%/125° C.), the sensing current I from the first drain D1 is much greater than 0, and the air extractor is activated to lower the humidity of the environment, so as to protect the electric apparatus 1000A.

In conclusion to the above, the electric apparatus according to an embodiment of the invention has a thin film transistor having a metal oxide semiconductor layer as a humidity sensor, allowing the electric apparatus according to an embodiment of the invention to have dual functions of displaying and sensing humidity of an environment. In addition, manufacturing processes of the humidity sensor and the active devices in the active area may be integrated, thereby simplifying the manufacturing process of the electric apparatus.

In addition, the electric apparatus according to an embodiment of the invention further includes a warning indicator or a protection system, so as to actively notify a user or to directly act to lower humidity of an environment.

Though the invention has been disclosed above by the embodiments, they are not intended to limit the invention. It will be apparent to one of ordinary skill in the art that modifications and variations to the described embodiments may be made without departing from the spirit and scope of the invention. Therefore, the protecting range of the invention falls in the appended claims.

What is claimed is:

1. An electric apparatus comprising:
  a display having an active area and a peripheral area connected to the active area, the display comprising:
    an active device array substrate having a plurality of active devices disposed in the active area;
    a humidity sensor disposed in the peripheral area, wherein the humidity sensor is a thin film transistor having a first metal oxide semiconductor layer, the humidity sensor further having a first gate overlapping with the first metal oxide semiconductor layer, and a first source and a first drain disposed at two opposite ends of the first metal oxide semiconductor layer and connected to the first metal oxide semiconductor layer, and wherein each of the active devices has a second gate, a second metal oxide semiconductor layer overlapping with the second gate, and a second source and a second drain disposed at two opposite ends of the second metal oxide semiconductor layer and connected to the second metal oxide semiconductor layer, wherein the first gate and the second gate belong to the same film layer, the first metal oxide semiconductor layer and the second metal oxide semiconductor layer belong to the same film layer, and the first source, the first drain, the second source and the second drain all belong to a film layer;

a passivation layer covering the active devices wherein the passivation layer at least exposes the first metal oxide semiconductor layer of the humidity sensor;

an opposite substrate disposed opposite to the active device array substrate;

a display medium disposed between the active device array substrate and the opposite substrate; and a process unit electrically connected to the humidity sensor and calculating a humidity value according to a sensing current from the humidity sensor.

2. The electric apparatus as claimed in claim 1, wherein the active device array substrate further has a temperature sensor disposed in the peripheral area and electrically connected to the process unit, the process unit calculating a temperature of the active device array substrate according to characteristics of the temperature sensor.

3. The electric apparatus as claimed in claim 2, wherein the temperature sensor is a metal wire surrounding the active area, and the process unit calculates the temperature of the active device array substrate according to a resistance value of the metal wire.

4. The electric apparatus as claimed in claim 3, wherein each of the active devices has a second gate, a second metal oxide semiconductor layer overlapping with the second gate, and a second source and a second drain disposed at two opposite ends of the second metal oxide semiconductor layer and connected to the second metal oxide semiconductor layer, wherein the metal wire and the second gate or the second source all belong to a film layer.

5. The electric apparatus as claimed in claim 2, wherein the humidity sensor further has a first gate overlapping with the first metal oxide semiconductor layer, and a first source and a first drain disposed at two opposite ends of the first metal oxide semiconductor layer and connected to the first metal oxide semiconductor layer.

6. The electric apparatus as claimed in claim 5, wherein the process unit provides a first gate voltage and a first source voltage respectively to the first gate of the humidity sensor and the first source of the humidity sensor according to the temperature of the active device array substrate, and the process unit calculates the humidity value according to the sensing current, the first gate voltage, the first source voltage, and the temperature of the active device array substrate, wherein the sensing current is transmitted to the first drain through the first metal oxide semiconductor layer.

7. The electric apparatus as claimed in claim 1, further including a warning indicator electrically connected to the humidity sensor and making corresponding reactions according to a value of the sensing current from the humidity sensor.

8. The electric apparatus as claimed in claim 7, wherein the warning indicator includes an indicator light or a buzzer.

9. The electric apparatus as claimed in claim 1, further including a protection system electrically connected to the humidity sensor and activated or deactivated according to a value of the sensing current from the humidity sensor.

10. The electric apparatus as claimed in claim 9, wherein the protection system is an air extractor.

\* \* \* \* \*